Jan. 16, 1951 F. MEILLAND Plant Pat. 1,001
ROSE PLANT
Filed Aug. 18, 1949
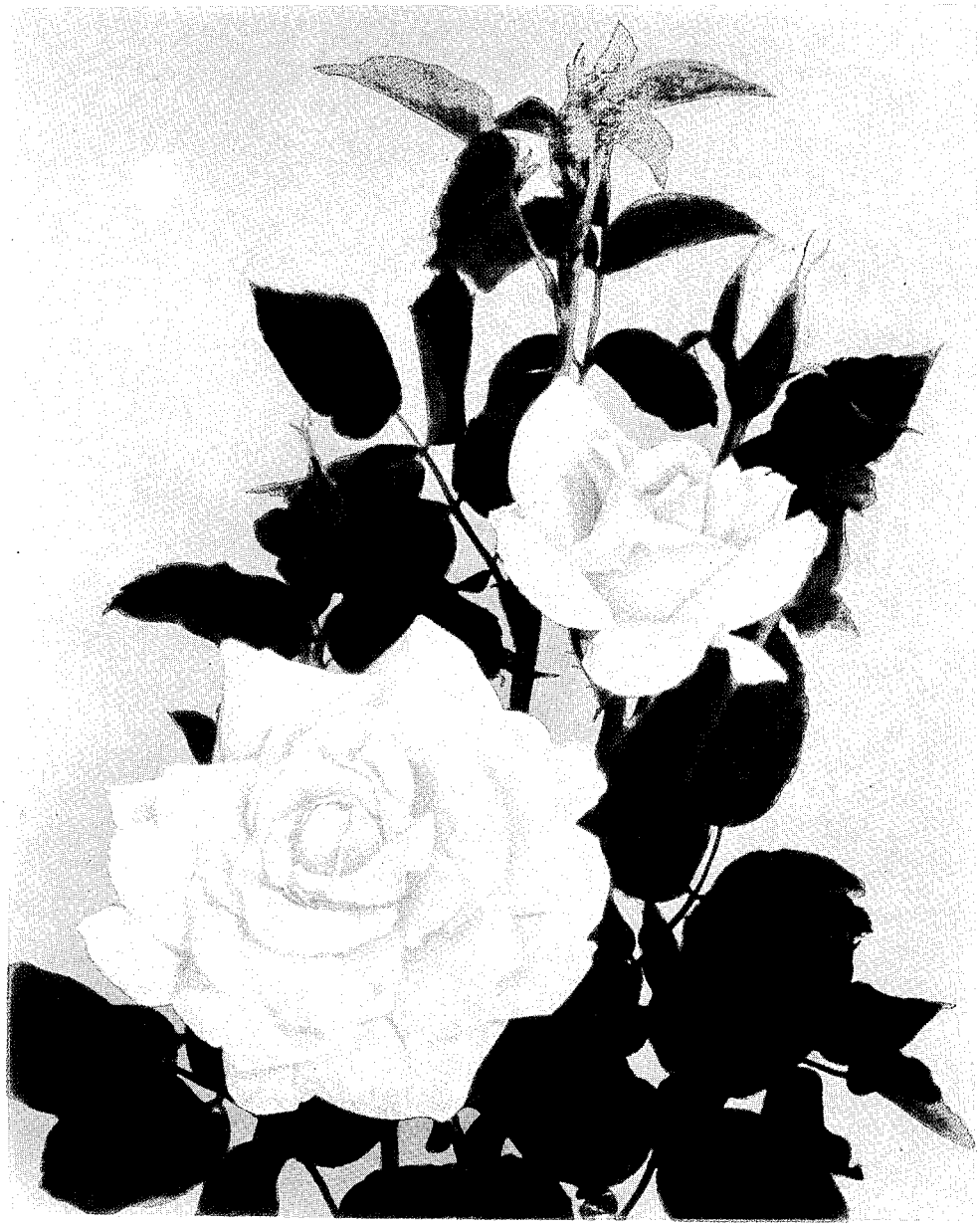
Inventor
F. Meilland
By Robb & Robb
Attorneys Patented Jan. 16, 1951

Plant Pat. 1,001

UNITED STATES PATENT OFFICE 1,001

ROSE PLANT

Francis Meilland, Cap Azura, Cap d' Antibes, France, assignor to The Conard-Pyle Company, West Grove, Pa., a corporation of Pennsylvania Application August 18, 1949, Serial No. 110,951

1 Claim. (Cl. 47—61)

This invention relates to a new and distinct variety of hybrid tea rose plant, the dominating and outstanding characteristic of which is that the flowers hold their very even yellow color well—better than any other yellow rose yet introduced, as far as I know.

Furthermore, the appearance of the plant is greatly enhanced by its abundant foliage. This combination of lasting pure, deep color of the yellow blooms and dense foliage is much more pronounced than in previous yellow hybrid tea roses and makes this new rose an especially desirable variety.

Asexual reproduction of this new variety shows the foregoing characteristics come true to form and are established.

In the drawings are shown specimens of the new variety at different stages of development of both the blossoms and the foliage.

This new variety was asexually reproduced by budding at Cap d'Antibes, France, and at West Grove, Pennsylvania.

The following is a detailed description of the new variety, reference to color being in accordance with Ridgway's Color Standards and Nomenclature where indicated and otherwise in accordance with the usual dictionary meaning.

Type: Hardy; bush; outdoor; seedling; for cut flowers and garden decoration.
Class: Hybrid tea.
Parentage: Léonce Colombier (unpatented) crossed with an unnamed seedling of Mme. Joseph Perraud (unpatented).
Propagation: Holds its distinguishing characteristics through succeeding propagations.

*Flower*

Locality where grown: West Grove, Pennsylvania.
Flowers borne: Singly to stem; on normal, medium length stems.
Quantity of bloom: Free; outdoors.
Continuity: continuous.
Fragrance: Slight; tea.

Bud:

*Peduncle.*—Medium length; medium heavy; erect; stiff; medium rough; medium number of red prickles. Color—light Oil Green, Plate V.

*Before calyx breaks.*—Size—medium. Form—medium length; pointed; ovoid; with foliaceous appendages on the surface of the bud; with medium cut foliaceous parts extending beyond the tip of the bud equal to one-fourth or more of its length.

*As calyx breaks.*—Color—Strontian Yellow, Plate XVI, with tinges of Strawberry Pink, Plate I.

*As first petal opens.*—Size—medium. Form—medium length; ovoid. Color—outside: Pinard Yellow, Plate IV; sometimes with tinges of Geranium Pink, Plate I; inside: Pinard Yellow, Plate IV.

*Opening.*—Opens up well.

Bloom: Size, when fully open—medium large; 3¾ inches to 4¼ inches.

*Petalage.*—Double to very double; from 25 to 35 petals; arranged regularly.

*Form.*—High centered at first; remaining high centered; petals being at first cupped inward with edges loosely curved outward; becoming later, at maturity, loosely rolled outward.

Petals: Medium thick; with inside and outside satiny.

*Shape.*—Outer—obovate. Intermediate—obovate. Inner—obovate.

*Color.*—Colors may be modified by having outer petals, occasionally, tinged with Strawberry Pink, Plate I; and by having the color at the base of the petals somewhat deeper and brighter than over the rest of the petal.

This description of a newly opened flower was made from a rose grown outdoors in the month of July, at West Grove, Pennsylvania:

*Color.—Outer petal*—outside surface: Pinard Yellow, Plate IV; inside surface: Pinard Yellow, Plate IV. *Intermediate petal*—outside surface: Pinard Yellow, Plate IV; inside surface: Pinard Yellow, Plate IV. *Inner petal*—outside surface: Pinard Yellow, Plate IV; inside surface: Pinard Yellow, Plate IV.

This description was made from a rose that was open for three days outdoors in the month of July, at West Grove, Pennsylvania:

*Color.—Outer petal*—outside surface: light Baryta Yellow, Plate IV; inside surface: Martius Yellow, Plate IV. *Inner petal*—outside surface: Pinard Yellow, Plate IV; inside surface: Pinard Yellow, Plate IV.

*General color effect.*—Newly opened flower—Pinard Yellow, Plate IV. Three days open—Pinard Yellow, Plate IV.

*Behavior.*—Drop off cleanly.

*Flower longevity.*—Cut roses grown outdoors kept at living room temperatures—3 to 5 days in July.

*Reproductive organs*

Stamens: Many; arranged regularly about pistils.
Filaments: Most with anthers of various lengths; *outer filaments* medium long; inner filaments short; yellow.
Anthers: Most open at once: medium size; yellow-orange; occasionally an anther fused with a petaloid or pistil.
Pollen: Moderate; yellow-orange.
Pistils: Many.
Styles: Uneven; medium length; medium heavy; bunched.
Stigma: Yellowish white.
Ovaries: All enclosed in calyx.
Hips: Ovoid to oblong; smooth; walls medium thin. Color—Parrot Green, Plate VI.
Sepals: Permanent; medium length; spear shaped.
Seeds: None found at time of description.

*Plant*

Foliage:
*Leaves.*—Compound of five leaklets; abundant; medium large; leathery.
*Leaflets.*—Oval with apex acute; base round; margin simply serrate.
*Color.*—*Mature*—upper surface: Dark Cress Green, Plate XXXI; under surface: Deep Grape Green, Plate XLI. *Young*—upper surface: dark Madder Brown, Plate XIII; Yellowish Oil Green, Plate V, along midrib; under surface: Vandyke Red, Plate XIII.
*Rachis.*—Medium heavy. Upper side: Grooved; under side: Sparsely to moderately thorny.

*Stipules.*—Medium length; narrow; with short points; turning out at an angle of more than 45°.
*Disease.*—Resistant to mildew and blackspot.
Growth:
*Habit.*—Bushy; upright; branched.
*Growth.*—Vigorous.
*Canes.*—Medium heavy.
*Main stems.*—Gray-green.
*Thorns*—many; medium length; straight; with medium length oval base. *Prickles and hairs*—none.
*Branches.*—Gray-green. *Thorns*—several; medium length; straight; with medium length narrow oval base; sometimes with incipient thorns among larger thorns. *Prickles*—few to several. *Hairs*—none.
*New shoots.*—Lettuce Green, Plate V, occasionally with reddish tinges. *Thorns*—several; medium length; straight; with medium length narrow oval base. Seldom with incipient thorns among larger thorns. *Pickles*—several. *Hairs*—none.

I claim:

A new and distinct variety of rose plant characterized as to novelty by its well formed buds; the clear, even, rich yellow color of the flowers that persists throughout their entire life; and the abundance of its large, handsome foliage, substantially as shown and described.

FRANCIS MEILLAND.

No references cited.